United States Patent [19]

Quinn et al.

[11] 4,282,391

[45] Aug. 4, 1981

[54] CONTINUOUS PROCESS FOR PRODUCING HALOGENATED DIPHENOLS

[75] Inventors: Clayton B. Quinn, Mt. Vernon, Ind.; Charles A. Wilson, II, Greenville, S.C.

[73] Assignee: General Electric Company, Mt. Vernon, Ind.

[21] Appl. No.: 101,841

[22] Filed: Dec. 10, 1979

Related U.S. Application Data

[63] Continuation of Ser. No. 882,192, Feb. 28, 1978.

[51] Int. Cl.³ .................. C07C 39/16; C07C 43/23; C07C 39/00
[52] U.S. Cl. .................. 568/726; 568/48; 568/56; 568/65; 568/637; 568/638; 568/725; 568/587; 568/588
[58] Field of Search ............... 568/33, 48, 65, 74, 568/637, 638, 725, 726

[56] References Cited

U.S. PATENT DOCUMENTS

| | | | |
|---|---|---|---|
| 3,143,575 | 8/1964 | Bryner et al. | 568/726 |
| 3,546,302 | 12/1970 | Asadarian et al. | 568/726 |
| 4,075,119 | 2/1978 | Schmidt et al. | 568/726 |
| 4,137,421 | 1/1979 | Li | 568/725 |
| 4,182,838 | 1/1980 | Mark et al. | 568/726 |
| 4,210,765 | 7/1980 | Mark | 568/726 |

FOREIGN PATENT DOCUMENTS

2520316  11/1976  Fed. Rep. of Germany ........... 568/726

*Primary Examiner*—Werren B. Cone
*Attorney, Agent, or Firm*—Martin B. Berancik; William F. Mufatti

[57] ABSTRACT

A continuous process for obtaining highly pure, high molecular weight aromatic polycarbonates from highly pure, halogenated diphenols.

8 Claims, 1 Drawing Figure

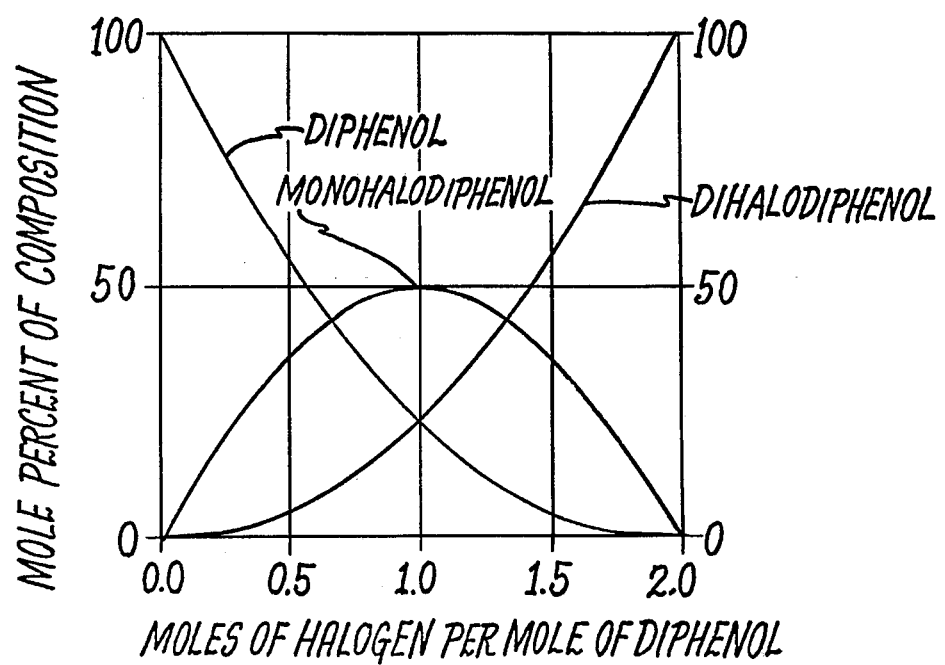

CONTINUOUS PROCESS FOR PRODUCING HALOGENATED DIPHENOLS

This is a continuation of application Ser. No. 882,192, filed Feb. 28, 1978.

This invention relates to a continuous process for halogenating diphenols which are used to manufacture high molecular weight aromatic polycarbonates and to the halogenated diphenols and polycarbonates obtained therefrom.

BACKGROUND OF THE INVENTION

The preparation of halophenols is customarily carried out by direct halogenation with elemental chlorine and/or bromine. In the case of simple or stable molecules, this appears to be the simplest process. However, when it is applied to more complicated and sensitive structures, it often yields by-products that can seriously interfere with the intended end-use of the halophenols. For instance, U.S. Pat. No. 3,062,781 discloses halogenated diphenols which are obtained by a direct halogenation procedure which require further treatment with sodium hydroxide and triethylamine at 80° C. before they can be converted to polycarbonates of acceptable stability. Such a treatment is necessary in order to remove aliphatically bound halogens formed in the halogenation process. It has been found that these aliphatically bound halogen compounds, which are generally recognizable by their red color, are formed by the cleavage reaction exerted by the hydrogen halide coproduct on the diphenol. For example, when 4,4'-isopropylidenediphenol (BPA) is employed, the chlorination reaction produces an equimolar amount of hydrogen halide coproduct as shown below wherein X represents a halogen:

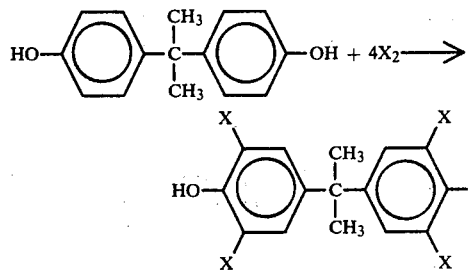

(I)

The HX coproduct produced in (I) above effects a cleavage reaction on BPA or its halogenated derivatives as shown below:

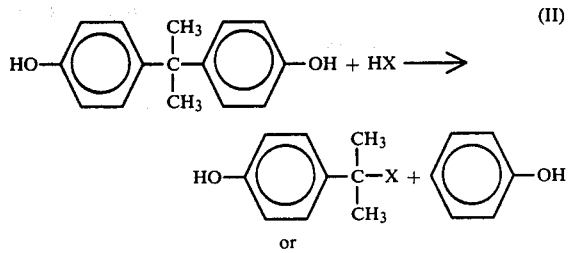

(II)

or

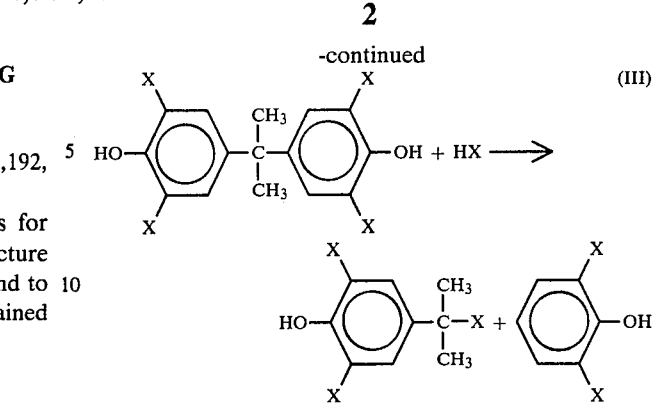

(III)

Thus, the haloisopropylphenols cause the discoloration and the halogenated phenols also have a disagreeable odor. The formation of by-products is even more pronounced when bromine is employed.

German Patent No. P25 20 317.2 discloses two methods for brominating and/or chlorinating bisphenols; namely, a gas-solid phase method and a suspension method. From these methods, there are obtained a mixture of unreacted bisphenol and statistical mixtures of halogenated bisphenols which are used to prepare polycarbonates having improved fire retardant properties.

In the suspension method disclosed in this German patent, the bisphenol is suspended in a halogen-containing hydrocarbon to produce a halogenated bisphenol. The halogen-containing hydrocarbons disclosed are carbon tetrachloride and tetrachloroethane, carbon tetrachloride being preferred.

While the suspension method disclosed in the above-identified German patent is of interest, it is not entirely satisfactory. For example, since bisphenols are not very soluble in either carbon tetrachloride or tetrachloroethane, excess halogen, i.e., either bromine and/or chlorine, must be used to assure halogenation of the bisphenols. As a result, a significant amount of halogen is lost in the system during the reaction and the rate of halogenation cannot be closely controlled. Thus, this method produces an excess of unreacted bisphenols and, primarily, tri- and tetrahalogenated bisphenols which, when further processed to produce a polycarbonate, do not impart good impact properties to the polycarbonate. Furthermore, the halogenated bisphenols must be isolated from the solvent system before they can be subjected to polymerization to obtain polycarbonates.

Co-pending application Ser. No. 882,191, filed Feb. 28, 1978, and assigned to the same assignee as this case, discloses a process for halogenating diphenols wherein the diphenol is dissolved or suspended in methylene chloride and a halogen gas is metered into the suspension to react with the diphenol. An inert gas is concurrently fed into the system and serves to purge the hydrogen halide produced thereby minimizing the formation of undesirable by-products.

Co-pending application Ser. No. 882,242, filed Feb. 28, 1978, and also assigned to the same assignee as this case, discloses a process for halogenating diphenols wherein the diphenol is dissolved or suspended in methylene chloride and then contacted with sulfuryl chloride. In addition to supplying chlorine, the sulfuryl chloride also reacts with the hydrogen halide produced in a "self-sweeping" reaction thereby minimizing the formation of undesirable by-products.

SUMMARY OF THE INVENTION

It has now been found that a halogenated diphenol can be prepared by dissolving or suspending the diphenol in a solvent system comprising methylene chloride and water and thereafter introducing a halogen into the solvent system. Since this process results in minimizing impurities and the formation of undesirable by-products, the highly pure halogenated diphenol obtained does not have to be treated further. Thus, the highly pure halogenated diphenol obtained is then reacted directly with a carbonate precursor to produce highly pure, high molecular weight aromatic polycarbonates.

The process of this invention is continuous with regard to producing either halogenated monomers or aromatic polycarbonates comprising these halogenated monomers. Furthermore, the process of the invention is based on using quantitative amounts of reactants enabling the reactions to be closely controlled. As a result, all of the halogen used is reacted with the monomer so that there is realized not only a savings in material and labor cost, but a savings in time as well as increased polycarbonate yield.

In the solvent system of the present invention, either chlorobenzene or methylene chloride can be used. However, methylene chloride is preferred for the primary solvent system material and is present in amounts, based upon the weight ratio of methylene chloride:diphenol, in the range of about 2:1–6:1, preferably, 4:1. Since only dissolved diphenol can be halogenated, the use of methylene chloride permits more rapid dissolution of diphenol in it. As a result, virtually all of the phenol can be reacted.

Water is the second part of the solvent system and serves to neutralize the hydrogen halide produced during halogenation. Water is present at a weight ratio of water:diphenol in the range of about 2:1–5:1, preferably 2.5:1.

As the halogen is introduced into the solvent system, aqueous caustic such as sodium hydroxide is concurrently added to control the pH level of the solvent system. Therefore, it is important that the mixture be quickly, thoroughly and well stirred to not only neutralize the hydrogen halide produced, but to also prevent the occurrence of undesirable side reactions.

During this reaction, the temperature of the solvent system can be about 0°–80° C., but is preferably held at about ambient temperature; i.e., 20°–40° C.

As the halogen is added to the solvent system, the pH of the reaction mixture is maintained below about pH 5, generally between pH 2–5 and preferably at pH 4. Above pH 5, undesirable side reactions are more likely to occur.

The amount of halogen added can vary depending upon the degree of halogenation desired. Thus, halogen can be added in amounts of about 0.1–2.0 or more moles per mole of diphenol present in the solvent system. Usually, halogen is added in amounts of about 1.0–1.5 moles, preferably about 1.2–1.35 moles per mole of diphenol. While any of the halogens can be employed, chlorine and bromine are preferred.

Completion of the reaction can be predetermined based upon the amount of halogen added to the solvent system or it can be determined by the absence of further production of hydrohalide acid and no increase or decrease in the pH level.

The halogenation reaction of the process of the invention can be represented by the following general equation:

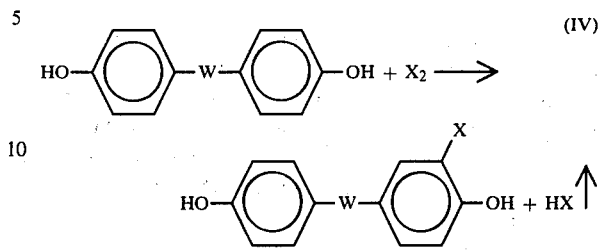

(IV)

By minimizing the undesirable co-product, HX, the formation of deleterious by-products, illustrated by the following general equation, is also minimized.

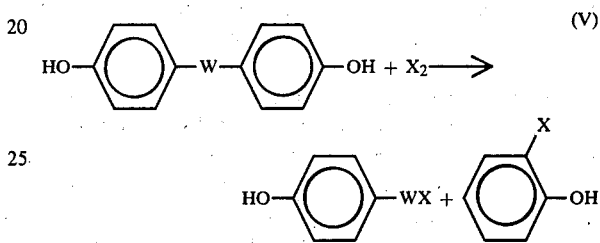

(V)

Accordingly, the halogenated diphenols produced using the process of this invention can be represented by the following general formula:

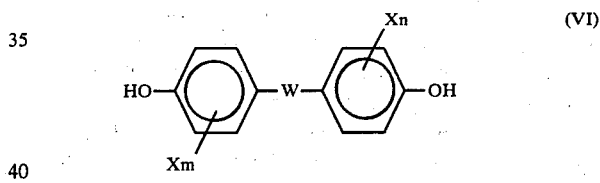

(VI)

wherein $X_m$ and $X_n$ can each be a halogen and mixtures thereof; m and n are each 0–2 with the proviso that $m+n$ equal at least 0.1, but no more than about 2; and, W is a member selected from the following group:

(a)

wherein r is 0–10 with the proviso that when both $X_m$ and $X_n$ are chlorine and m and n are each 1, r is 0 or 2–10;

(b)

wherein R is a member of the group consisting of $C_1$–$C_{10}$ alkyl and $C_6$–$C_{14}$ aryl;

(c)

wherein R and R' can each independently be the same as R in (b) above;

(d)

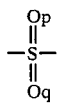

wherein p and q can each independently be 0–1; and, (e) —O—.

W is the same in the formulas for equations IV and V as described for formula VI.

In producing the diphenol of formula IV wherein W can be (a), (b) or (c), particularly (c), the formation of deleterious by-products is especially pronounced when employing prior art processes. When the process of this invention is employed, however, the formation of such deleterious by-products is significantly minimized. Thus, the halogenated diphenols produced in accordance with this invention are virtually colorless or white as compared to the discolored halogenated diphenols obtained by prior art processes.

Since the halogenation reaction in the process of the invention is based upon quantitative consumption of halogen, the process enables the degree of halogenation of the diphenol to be closely controlled. Accordingly, predetermined statistical mixtures of unreacted diphenol and reacted diphenol can be readily obtained. The amount of each obtained depends upon the moles of halogen added.

As can be seen from the FIGURE, a statistical maximum of 50 mole percent of monohalodiphenol obtains at a mole ratio of halogen:diphenol of 1:1, whereas a statistical maximum of essentially 100 mole percent dihalodiphenol obtains at a mole ratio of halogen-diphenol of 2:1. Accordingly, it is possible to produce essentially 100% of pure dihalodiphenol. Alternatively, statistical ternary mixtures comprising unreacted diphenol, monohalodiphenol and dihalodiphenol can be obtained as shown by the FIGURE. This also pertains when mixtures of halogens are employed.

DETAILED DESCRIPTION OF THE INVENTION

Typical of some of the diphenols that can be employed in this invention are bisphenol-A (2,2-bis(4-hydroxyphenyl)propane), bis(4-hydroxyphenyl)methane, 2,2-bis(4-hydroxy-3-methylphenyl)propane, 4,4-bis(4-hydroxyphenyl)heptane, 1,1-bis(4-hydroxyphenyl)ethane, 3-methyl-2,2-bis(4-hydroxyphenyl)propane, bis-(4-hydroxyphenyl)sulfone, bis-(4-hydroxyphenyl)ether, and the like. Other non-halogenated diphenols of the bisphenol type can also be used such as are disclosed in U.S. Pat. Nos. 2,999,835, 3,028,365 and 3,334,154.

Of course, it is possible to employ two or more different monomers or a copolymer with a glycol or with hydroxy or acid terminated polyester, or with a dibasic acid in the event a carbonate copolymer or interpolymer rather than a homopolymer is desired for use in preparing the aromatic polycarbonate. Blends of any of these materials can also be used to obtain the aromatic polycarbonates.

These high molecular weight aromatic polycarbonates can be linear or branched homopolymers or copolymers as well as mixtures thereof or polymeric blends and generally have an intrinsic viscosity (IV) of about 0.40–1.0 dl/g as measured in methylene chloride at 25° C. These high molecular weight aromatic polycarbonates can be typically prepared by reacting a bisphenol with a carbonate precursor.

The carbonate precursor used can be either a carbonyl halide, a carbonate ester or a haloformate. The carbonyl halides can be carbonyl bromide, carbonyl chloride and mixtures thereof. The carbonate esters can be diphenyl carbonate, di-(halophenyl) carbonates such as di-(chlorophenyl) carbonate, di-(bromophenyl) carbonate, di-(trichlorophenyl) carbonate, di-(tribromophenyl) carbonate, etc., di-(alkylphenyl) carbonates such as di(tolyl) carbonate, etc., di-(naphthyl) carbonate, di-(chloronaphthyl) carbonate, phenyl tolyl carbonate, chlorophenyl chloronaphthyl carbonate, etc., or mixtures thereof. The haloformates that can be used include bis-haloformates of dihydric phenols (bischloroformates of hydroquinone, etc.) or glycols (bishaloformates of ethylene glycol, neopentyl glycol, polyethylene glycol, etc.).

While other carbonate precursors will occur to those skilled in the art, carbonyl chloride, also known as phosgene, is preferred.

Also included are the polymeric derivatives of a dihydric phenol, a dicarboxylic acid and carbonic acid such as are disclosed in U.S. Pat. No. 3,169,121 which is incorporated herein by reference.

Molecular weight regulators, acid acceptors and catalysts can also be used in obtaining the aromatic polycarbonates of this invention. The useful molecular weight regulators include monohydric phenols such as phenol, chroman-I, paratertiarybutylphenyl, parabromophenol, primary and secondary amines, etc. Preferably, phenol is employed as the molecular weight regulator.

A suitable acid acceptor can be either an organic or an inorganic acid acceptor. A suitable organic acid acceptor is a tertiary amine such as pyridine, triethylamine, dimethylaniline, tributylamine, etc. The inorganic acid acceptor can be either a hydroxide, a carbonate, a bicarbonate, or a phosphate of an alkali or alkaline earth metal.

The catalysts which can be employed are those that typically aid the polymerization of bisphenol-A with phosgene. Suitable catalysts include tertiary amines such as triethylamine, tripropylamine, N,N-dimethylaniline, quaternary ammonium compounds such as, for example, tetraethylammonium bromide, cetyl triethyl ammonium bromide, tetra-n-heptylammonium iodide, tetra-n-propyl ammonium bromide, tetramethylammonium chloride, tetramethyl ammonium hydroxide, tetra-n-butyl ammonium iodide, benzyltrimethyl ammonium chloride and quaternary phosphonium compounds such as, for example, n-butyltriphenyl phosphonium bromide and methyltriphenyl phosphonium bromide.

Also included herein are branched polycarbonates wherein a polyfunctional aromatic compound is reacted with the bisphenol and carbonate precursor to provide a thermoplastic randomly branched polycarbonate. These polyfunctional aromatic compounds contain at least three functional groups which are carboxyl, carboxylic anhydride, haloformyl, or mixtures thereof. Illustrative of polyfunctional aromatic compounds which can be employed include trimellitic anhydride, trimellitic acid, trimellityl trichloride, 4-chloroformyl phthalic anhydride, pyromellitic acid, pyromellitic dianhydride, mellitic acid, mellitic anhydride, trimesic acid, benzophenonetetracarboxylic acid, benzophenonetetracarboxylic anhydride, and the like. The preferred polyfunctional aromatic compounds are trimellitic anhydride and trimellitic acid or their acid halide derivatives.

The high molecular weight aromatic polycarbonate compositions of the invention are prepared by halogenating the monomer at pH 2–5, followed by reacting the halogenated monomer with a carbonate precursor which, when carbonyl chloride is used, is known as "phosgenation", then adjusting the pH of the resultant reaction product to about 11 to 11.5 in a water solution and in the presence of a catalyst to obtain a high pure, high molecular weight aromatic polycarbonate.

Obviously, other materials can also be employed with the aromatic polycarbonate of this invention and include such materials as anti-static agents, plasticizing agents, pigments, thermal stabilizers, ultraviolet stabilizers, reinforcing fillers and the like.

Accordingly, the highly pure, high molecular weight aromatic polycarbonates of the invention can be represented by the following general formula:

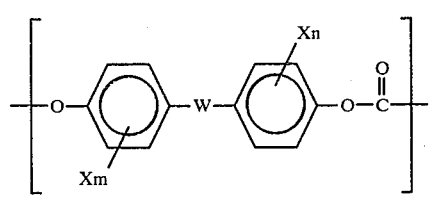

(VII)

wherein $X_m$, $X_n$, n and W are the same as identified above and wherein said polycarbonate has an intrinsic viscosity (IV) of about 0.4–1.0 dl/g in methylene chloride at 25° C.

PREFERRED EMBODIMENT OF THE INVENTION

The following examples are set forth to more fully and clearly illustrate the present invention and are intended to be, and should be construed as being, exemplary and not limitative of the invention. Unless otherwise stated, all parts and percentages are by weight.

EXAMPLE 1

To a ten (10) gallon reactor vessel fitted with reflux condenser, caustic addition equipment, phosgene and chlorine addition equipment, agitator and pH electrode, there was added 10 moles (about 5 lbs.) of bisphenol-A (2,2-bis(4-hydroxyphenyl) propane), 7 liters (about 20 lbs.) methylene chloride ($CH_2Cl_2$), and 5.7 liters (about 12 lbs.) water. As this mixture was being well stirred, there was added, over a 30 minute period, 10 moles of chlorine gas while the pH was controlled between pH 2–5 by the addition of aqueous caustic. After chlorination was completed, the pH of the mixture was adjusted to pH 11 and 14 ml. of triethylamine (TEA) was added together with 18.8 g. phenol as a chain terminator, 3.4 g. sodium gluconate, and 5 liters of water. This mixture was then phosgenated by reacting it with 1080 g. (about 2.38 lbs.) carbonyl chloride over a period of 30 minutes, while the pH was controlled at 11.0 to 11.5 with aqueous caustics. This mixture was diluted with 7 liters methylene chloride and phase separated to remove the brine solution produced during reaction. The methylene chloride phase was washed twice with 0.01 N HCl, and washed three times with water. The resultant polymer was isolated from the methylene chloride solution by precipitation using high pressure steam (pressure of about 125–150 psi) followed by drying in a nitrogen purged fluid bed dryer at a temperature of 100°–125° C. for a period of 24 hours to yield a white polycarbonate powder having an IV in $CH_2Cl_2$ at 25° C. of 0.53 dl/g.

EXAMPLE 2

The same procedure was followed as in Example 1 except that 12 moles of chlorine gas and 16.9 g. phenol were used. There was obtained a white polycarbonate resin having an IV of 0.50 dl/g.

EXAMPLE 3

The same procedure and the same amounts of reactants were used in this example as were employed in Example 2 except that after 432 g. phosgene had been added, 12.0 g. of trimellitic trichloride was also added as a branching agent. There was obtained a white polycarbonate resin having an IV of 0.54 dl/g.

EXAMPLE 4

The same procedure was followed as in Example 1 except that 15 moles chlorine gas was used and, after chlorination, 9.4 g. phenol was added. There was obtained a white polycarbonate resin having an IV of 0.45 dl/g.

EXAMPLE 5

The same procedure was followed as in Example 1 except that 12.36 moles bromine gas were added over a period of 140 minutes and the pH was controlled at about pH 4 by the addition of 10% aqueous caustic. After bromination, 9.4 g. phenol and 3.4 g. sodium gluconate were added to the reaction mixture. Phosgenation occurred over a period of 37 minutes. After phase separation, the $CH_2Cl_2$ was washed once with aqueous HCl, then twice with water. There was obtained a white polycarbonate resin having an IV of 0.36 dl/g.

EXAMPLE 6

A 4-neck, 2-liter round bottom flask was fitted with a mechanical stirrer, reflux condenser, pH electrode, automatic caustic addition inlet valve, and bromine-chlorine addition line. To the reactor was added 114 g. (0.5 mole) of bisphenol-A (2,2-bis(4-hydroxyphenyl) propane), 350 ml of methylene chloride, and 275 ml of water. To a side arm test tube was added 40 g. (0.25 mole) of bromine. The side arm of the test tube was attached to the reaction vessel and 17.35 g. (0.25 mole) of chlorine with a slow nitrogen sweep was bubbled into the bromine. The bromine-chlorine combination was swept into the reaction vessel while maintaining a pH between 2 and 5 over a 1 hour period. After bromination-chlorination was complete, the pH was raised to 11 and 1.5 g. phenol and 0.7 ml of triethylamine was added to the reactor. The mixture was phosgenated with 60 g. of carbonyl chloride over a period of 30 minutes. The polymer solution was then phase separated as in Example 1 and the $CH_2Cl_2$ phase was washed once with 0.01N HCl and four times with water. The polycarbonate was then precipitated into methanol and, after drying at 110° C. for 48 hours, there was obtained a white polycarbonate resin having an IV of 0.40 dl/g.

The monomer distribution of each of the polycarbonates obtained in Examples 1–6 was determined by gas chromatography and the results are set forth in Table I.

In addition, the flame retardancy of each of the polycarbonates obtained in Examples 1–6 was also determined. The polycarbonates were each fed to an extruder which was operated at about 265° C. and the extrudates were each comminuted into pellets.

The pellets were then injection molded at about 315° C. into test bars of about 5 in. by ½ in. by about 1/16–⅛ in. thick. The test bars (5 for each polycarbonate) were then subject to the test procedure set forth in Underwriters' Laboratories, Inc. Bulletin UL-94, Burning Test for Classifying Materials. In accordance with this test procedure, materials so investigated are rated either V-O, V-I or V-II based on the results of 5 specimens. The criteria for each V (for vertical) rating per UL-94 is briefly as follows:

"V-O": Average flaming and/or glowing after removal of the igniting flame shall not exceed 5 seconds and none of the specimens shall drip flaming particles which ignite absorbent cotton.

"V-I": Average flaming and/or glowing after removal of the igniting flame shall not exceed 25 seconds and the glowing does not travel vertically for more than ⅛" of the specimen after flaming ceases and glowing is incapable of igniting absorbent cotton.

"V-II": Average flame and/or glowing after removal of the igniting flame shall not exceed 25 seconds and the specimens drip flaming particles which ignite absorbent cotton.

In addition, a test bar which continues to burn for more than 25 seconds after removal of the igniting flame is classified, not by UL-94, but by the standards of the instant invention, as "burns". Further, UL-94 requires that all test bars in each test group must meet the V type rating to achieve the particular classification. Otherwise, the 5 bars receive the rating of the worst single bar. For example, if one bar is classified as V-II and the other four (4) are classified as V-O, then the rating for all bars is V-II. The results obtained are set forth in Table II wherein the "Control" denotes a non-halogenated polycarbonate resin.

TABLE I

Monomer Distribution in Polycarbonate Resins

| Example | Unreacted BPA (wt. %) | Monohalo BPA (wt. %) Cl | Monohalo BPA (wt. %) Br | Dihalo BPA (wt. %) Cl | Dihalo BPA (wt. %) Br | Tri- & Tetra-halo BPA (wt. %) Cl | Tri- & Tetra-halo BPA (wt. %) Br |
|---|---|---|---|---|---|---|---|
| 1 | 28.5 | 25.6 | — | 45.9 | — | — | — |
| 2 | 22.0 | 30.3 | — | 47.7 | — | — | — |
| 3 | 21.3 | 30.6 | — | 48.0 | — | — | — |
| 4 | 3.7 | 37.1 | — | 58.1 | — | — | — |
| 5 | 33.7 | — | 22.0 | — | 41.4 | — | 2.9 |
| 6 | 29.9 | 11.3 | 30.6 | 11.2 | 17.0 | trace | trace |

The results set forth in Table I above further dramatically reveal not only how the degree of halogenation can be obtained through the process of this invention, but also the nature or type of halogenation; i.e., mono- and/or di-halogenation, in the polycarbonate of the invention.

TABLE II

Flame Retardancy of Polycarbonate Resins

| Example | UL-94 Rating |
|---|---|
| Control | V-II |
| 1 | V-0 |
| 2 | V-0 |
| 3 | V-0 |
| 4 | V-0 |
| 5 | V-0 |
| 6 | Not tested |

The results in Table II above reveal that the flame retardany of the highly pure polycarbonate resins of the invention are excellent.

What is claimed is:

1. A process for halogenating a diphenol which comprises
   dissolving or suspending a diphenol in a solvent system comprising water and a primary solvent system member selected from the group consisting of methylene chloride and chlorobenzene, the weight ratio of said primary solvent system member to said diphenol being in the range of about 2:1–6:1 and weight ratio of water to said diphenol being in the range of about 2:1–5:1;
   introducing a halogen into said solvent system, said halogen being introduced in an amount of about 0.1–2.0 moles per mole of said diphenol; and,
   maintaining the pH of said solvent system at about pH 2–5 to obtain a predetermined statistical mixture of unhalogenated, monohalogenated, and dihalogenated diphenol with substantially reduced quantities trihalo and tetrahol substituted diphenol.

2. The process of claim 1 wherein said member is methylene chloride.

3. The process of claim 1 wherein said diphenol is 2,2-bis(4-hydroxyphenoly)propane.

4. The process of claim 1 wherein the amount of halogen introduced is about 1.0–1.5 moles per mole of said diphenol.

5. The process of claim 1 wherein said solvent system is maintained at about pH 4.

6. The process of claim 2 wherein the weight ratio of methylene chloride:diphenol is about 4:1.

7. The process of claim 1 wherein the weight ratio of water:diphenol is about 2.5:1.

8. The process of claim 4 wherein said halogen is introduced in an amount of about 1.2–1.35 moles per mole of said diphenol.

* * * * *